US00PP12959P2

(12) United States Plant Patent
Drewlow

(10) Patent No.: US PP12,959 P2
(45) Date of Patent: Sep. 17, 2002

(54) GUINEA IMPATIENS PLANT NAMED 'OVATION BRIGHT WHITE'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/621,491

(22) Filed: Jul. 21, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Bright White, characterized by its white flower color, shiny dark green leaves, early flowering, and long-lasting flowering, self-branching and vigorous habit.

1 Drawing Sheet

1

The present invention relates to new and distinctive cultivar of Impatiens plant, botanically known as *Impatiens Hawkeri*, commercially known as New Guinea Impatiens, and known by the cultivar name 'Ovation Bright White'. Ovation Bright White was developed in a controlled breeding program by crossing Mikkelsen Seedling No. 94-693-1 (seed parent) with Mikkelsen Seedling No. 95-333-1 (pollen parent). The seed and pollen parents are proprietary breeding lines which have not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguishes the new Impatiens from both its parent varieties and other cultivated Impatiens of this type known and used in the floriculture industry:

1. Ovation Bright White is white flowered as are Moorea (U.S. Plant Pat. No. 9,147) and Harmony White (unpatented), however, both comparisons show a pink cast in the bud stage while Ovation Bright White buds stay pure white.

2. Ovation Bright White is more mounded in growth habit than Moorea and Harmony White, taller than Moorea and similar in height to Harmony White.

3. Ovation Bright White has small leaves being 9 to 10 cm long and 3 to 3.5 cm wide. Harmony White has leaves 10 to 11 cm long and 3.5 to 4 cm wide; Moorea has leaves 11 to 12 cm long and 4.0 to 4.5 wide, all based on average mature leaves.

4. Ovation Bright White has a light green spur on the flower while both comparisons have a spur with a reddish cast.

5. Ovation Bright White has the least amount of red pigmentation around the nodes on the stems, Harmony White with the most and Moorea intermediate.

6. Ovation Bright White has more flowers and carries them over leaf canopy better than Harmony White or Moorea when grown in full sun and high temperatures outside.

7. Ovation Bright White is 5 to 7 days eariler to flower than Moorea and is similar to Harmony White.

The accompanying colored photograph illustrates the overall appearance of this cultivar taken as a face view of the plant and showing the colors as true as it is reasonably possible to obtain in a colored reproduction of this type.

2

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and with nutritional trace elements added. Habit of growth, foliage coloration, leaf variegation, size of leaves and flower size will be greatly influenced by nutritional and environmental conditions.

Color references are made to The Royal Horticultural Society Colour Chart except where general terms of ordinary significance are used.

Parentage: A controlled cross between female parent Mikkelsen Seedling No. 94-693-1 and male parent Mikkelsen Seedling No. 95-333-1.

Propagation:

( A ) *Type cutting.*—Stem tip 15 mm long will develop to 4 to 5 cm long in 18 to 21 days.

( B ) *Time to root.*—8–10 days at 23° C. summer; 10–12 days at 20° C. winter.

( C ) *Rooting habit.*—Heavy, fibrous.

Plant description:

( A ) *Form and habit of growth.*—Mounded to semi-upright, self-branching, intermediate in height, flowers open over the top of leaf canopy; continuous flowering; vigorous growing flowering herb. Average plant height is 15 to 22 cm, and average width is 40 to 45 cm. Internode length is 6 to 7 cm, but is highly variable, with a color of Yellow-Green Group 146C.

( B ) *Foliage description.*—Shiny dark green leaves with whitish-green midrib and no leaf variegation. The young midrib underside is Yellow-Green Group 146D, and the mature midrib underside is Yellow-Green Group 148C. Mature leaf color is Yellow-Green Group 147A. Stem color is Yellow-Green Group 146C. (1) Size: 9 to 10 cm long and 3.0 to 3.5 cm wide on average mature leaf. (2) Shape: Lanceolate with acuminate apex and acute base. (3) Texture: Both upper and lower surfaces are glabrous.

(4) Margin: Entire, covered with fine ciliate. (5) Color: Young Foliage, top side is Yellow-Green Group 147A, underside is Yellow-Green Group 146B. Mature foliage, top side is Yellow-Green Group 147A, underside is Yellow-Green Group 147B. (6) Venation: Pinnate. Young and mature venation underside is Yellow-Green Group 146A.

(C) *Branching.*—Lateral branching at base: 5 or more. Lateral branch length is 12 to 15 cm, but is highly variable.

Flowering description:

(A) *Flowering habits.*—Flowers continuously from leaf whorl in a progressively orderly manner with one flower per leaf axil. When the last flower in a whorl opens, the first flower in the leaf whorl above starts to open. It takes 5 to 7 days for a mature bud to fully open and the flower may last two weeks or longer depending on the environment. The time to first flower is 50 to 55 days from rooted cutting. The flowers are self-cleaning.

(B) *Normal flowering season.*—Indeterminate and continuous; quantity of flowering increases with increasing levels of light.

(C) *Flower bud.*—Ellipsoidial; flowers perfect; spur is Yellow-Green Group 148C and 4.0 cm long on mature bud, with the throat behind the ovary and originating from the major sepal. The spur tip is Yellow-Green Group 144A. The pedicel is Yellow-Green Group 148C, the throat is Yellow-Green Group 145C, and the bud is White Group 155C, just before opening.

(D) *Flowers borne.*—On individual light green pedicels 4.0 cm long from a whorl of usually five leaves. Flowering progressively around the whorls as buds and leaves develop. Leaf axils have one flower each.

(E) *Quantity of flowers.*—Numerous because of self-branching nature of plant and the long-lasting flower characteristic.

(F) *Diameter of flower.*—6.5 to 7.0 cm. Flower depth: 5 mm.

(G) *Petals.*—(1) Shape: Heart. (2) Color: Top side when opening is White Group 155C with no fading; underside is White Group 155C with Yellow-Green Group 145C around center of standard petal. (3) Number of petals: Five. (4) Size of petals: Standard: 4.5 cm wide and 3.0 cm long, two equal lobes with shallow cut. Wings: 3.5 cm wide and 3.5 cm long, two nearly equal lobes with shallow cut. Keel: 4.0 cm wide and 4.0 cm long, two unequal lobes with deep cut.

(H) *Reproductive organs.*—(1) Stamens: Five in number. (a) Anther: Hooded shape, White Group 155A. (b) Pollen color: Yellow-White Group 158D. (2) Pistils: (a) Stigma: Five, segmented column, White Group 155B. (b) Style color: White. (c) Ovaries: Five in number, size is 5 mm when immature, Yellow-Green Group 146A.

(I) *Fertility.*—The plants are fertile, but do not normally set seed under greenhouse conditions, unless in a controlled breeding program.

Disease resistance: No significant disease or insect problems seen to date.

OTHER IMPORTANT CHARACTERISTICS

1. Self-branching, early flowering nature allows cultivar to be grown in 10 cm pots but is also very vigorous enough to be grown in 15 to 25 cm containers as well.

2. Minimal fading of older flowers and large overlapping petals result in a round flower that produces an attractive floral display.

3. Has shown the ability to tolerate both high temperatures and full sun and continue to bloom as demostrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Bright White, as illustrated and described.

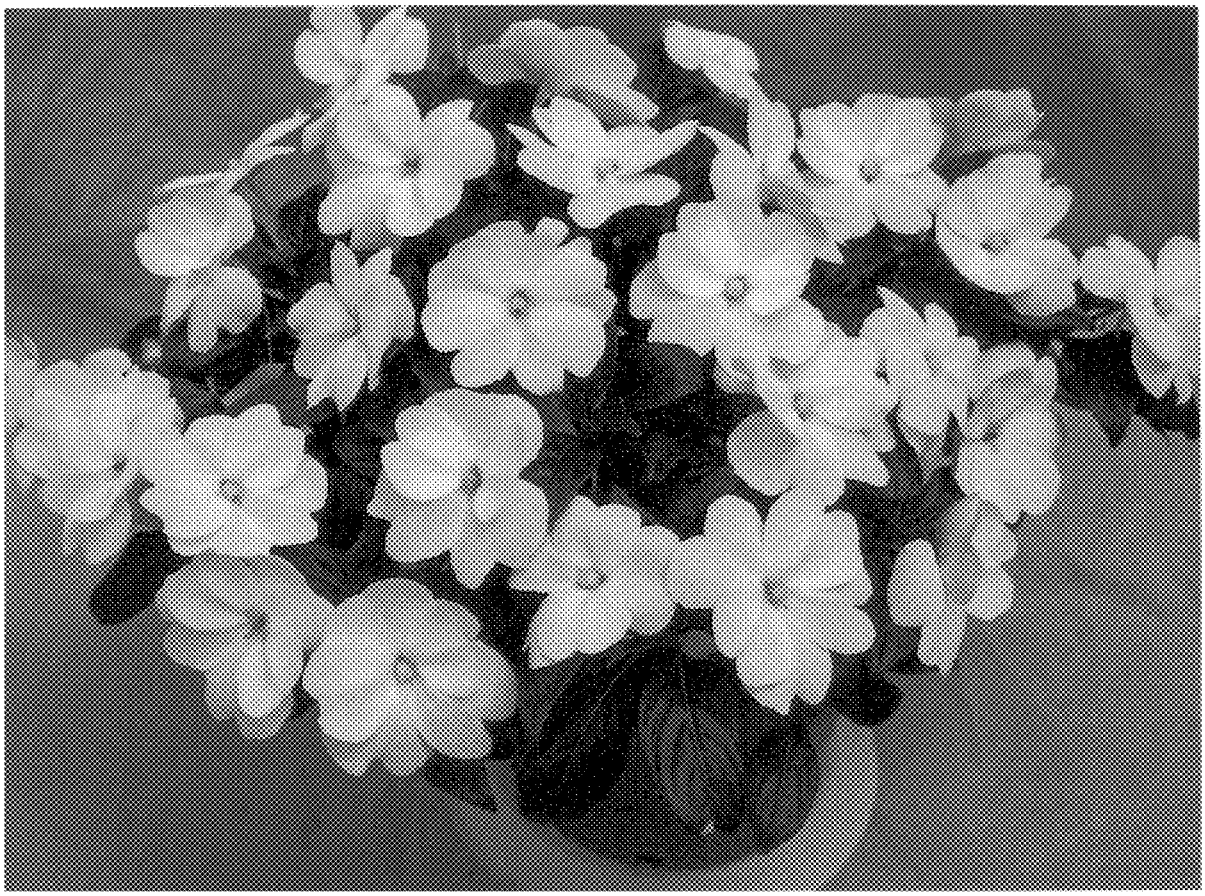

* * * * *